United States Patent [19]

Oediger et al.

[11] B 3,993,665

[45] Nov. 23, 1976

[54] 3-AMIDOCOUMARANONES

[75] Inventors: Hermann Oediger, Cologne; Rudolf Braden, Odenthal-Scheuren, both of Germany

[73] Assignee: Bayer Aktiengesellschaft, Germany

[22] Filed: Aug. 8, 1974

[21] Appl. No.: 495,554

[44] Published under the second Trial Voluntary Protest Program on February 3, 1976 as document No. B 495,554.

Related U.S. Application Data

[62] Division of Ser. No. 310,792, Nov. 30, 1972, Pat. No. 3,880,919.

[30] Foreign Application Priority Data

Dec. 17, 1971 Germany............................. 2172717

[52] U.S. Cl........................... 260/343.3 R; 424/279
[51] Int. Cl.²........................................ C07D 493/00
[58] Field of Search................................. 260/343.3

[56] References Cited

UNITED STATES PATENTS 2,473,484   6/1949   Ullyot.............................. 260/343.3

OTHER PUBLICATIONS

Wislicenus et al., Ber. v. 42, (1909), pp. 1930–1940.

*Primary Examiner*—James A. Patten

[57] ABSTRACT

3-Amidocoumaranones which may be substituted in the benzene ring by halo or alkyl; the compounds are obtained by treating an appropriate 2-hydroxyphenylacetic acid lactone with nitrous acid or with an ester, salt or chloride of nitrous acid in an acid medium to afford a coumaranedione-3-monoxime which is subjected to catalytic hydrogenation in the presence of an acid anhydride. The resulting 3-amidocoumaranone is an intermediate in the preparation of $\alpha$-amino-2-hydroxyphenylacetic acid which can be used to synthesize antibiotics such as cephalosporin and penicillin derivatives.

5 Claims, No Drawings

3-AMIDOCOUMARANONES

This is a division of application Ser. No. 310,792 filed Nov. 30, 1972, now U. S. Patent No. 3,880,919 issued Apr. 29, 1975.

DETAILED DESCRIPTION

The present invention relates to a process for the production of α-amino-2-hydroxyphenylacetic acids, which are known as intermediates for the synthesis of pharmaceuticals, particularly certain antibiotics as discussed below.

It is known that α-amino-2-hydroxyphenylacetic acid can be obtained by converting 2-methoxybenzaldehyde into the corresponding hydantoin with potassium cyanide and ammonium carbonate, demethylating this with hydriodic acid by heating, and saponifying the resulting 5-(2-hydroxyphenyl)-hydantoin with barium hydroxide; see, e.g. J. Org. Chem. 9 (1944), 21. The total yield however, is less than 20% so that this process is uneconomical in this regard. Furthermore, hydriodic acid is expensive when employed industrially. Finally, saponification with barium hydroxide is a complicated procedure since barium ions have to be removed, for example as the sparingly soluble sulphate, before isolating the desired pharmaceutical intermediate.

This invention now provides a process for the production of α-amino-2-hydroxyphenylacetic acids of the formula:

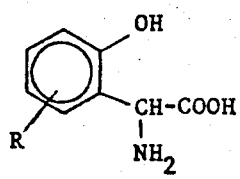

in which R is hydrogen, halogeno or alkyl of 1 to 4 carbon atoms.

According to the present process, a 2-hydroxyphenyl-acetic acid lactone of the formula:

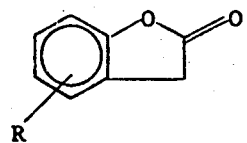

is reacted with nitrous acid, or a derivative of nitrous acid, in a solvent to produce a coumaranedione-3-monoxime of the formula:

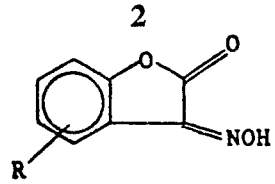

The coumaranedione-monoxime of Formula III is next catalytically hydrogenated in the presence of an acid anhydride of the formula:

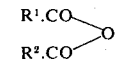

in which
$R^1$ and $R^2$ are the same or different alkyl group of 1 to 4 carbon atoms
to yield a 3-amidocoumaranone of the formula:

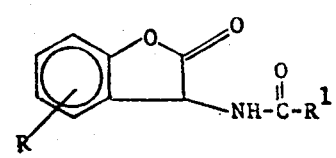

This 3-amidocoumaranone is finally hydrolyzed with dilute mineral acid to produce the desired α-amino-2hydroxyphenylacetic acid of Formula I.

While it is known that phenylacetic acid ethyl ester can be converted into the α-oximino derivative with ethyl nitrite in the presence of potassium ethylate; see e.g. Ber. d. dtsch. Chem. Gesellschaft, Vol. 42 (1909), page 1930, the process is technically complicated. Arylacetic acid ethyl esters in general have little tendency to react with nitrous acid; see e.g. Houben-Weyl-Muller, Vol. X/4, page 29. In contrast 2-hydroxyphenylacetic acid lactone reacts with nitrosylating agents in an acid medium smoothly, rapidly and in high yield to yield the coumaranedione-monoxime.

The individual reaction steps of the process according to the invention are technically simple to carry out and good yields are realized in each step. The α-amino-2-hydroxyphenylacetic acids are thus obtained in higher yields than according to the known process. In addition, the process permits the product to be produced industrially in a highly economical manner.

If, for example, 2-hydroxyphenylacetic acid lactone is used as the starting substance, sodium nitrite in glacial acetic acid is used as the donor of nitrous acid, acetic anhydride is used as the alkanoic acid anhydride, palladium-on-charcoal is used as the hydrogenation catalyst and hydrochloric acid is used as the hydrolyzing mineral acid, the course of the reaction can be diagrammatically depicted as follows:

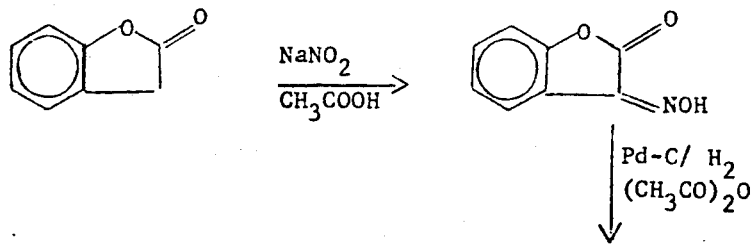

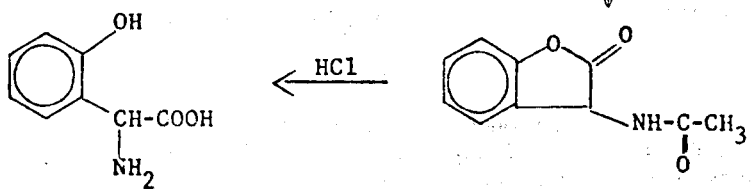

The 2-hydroxyphenylacetic acid lactones which are used as starting materials for the process according to the invention are either known or can be produced according to known processes, for example by splitting off water from the corresponding 2-hydroxyphenylacetic acids; see e.g. J. Amer. Chem. Soc. 82 (1960), 2035.

The nitrous acid derivatives which are used in the first stage of the reaction include lower alkyl esters, alkali metal salts and the chloride of nitrous acid. Lower alkyl esters are those alkyl esters having up to 6 carbon atoms, such as methyl nitrite, ethyl nitrite, n-butyl nitrite, amyl nitrite and the like. Sodium nitrite is particularly suitable for use as the alkali metal salt of nitrous acid. Nitrosyl chloride can also be used. Solvents for the reaction include ethers such as diethyl ether and aliphatic carboxylic acids having up to 6 carbon atoms as for example acetic acid and propionic acid. An acidic environment is advantageous. If nitrous acid esters are used in a neutral solvent, for example ether, hydrogen chloride is thus generally introduced into the reaction mixture in order to initiate the nitrosylation. A preferred combination is sodium nitrite in glacial acetic acid.

Typically, 1 mole of the 2-hydroxyphenylacetic acid lactone is reacted with 1.5 moles of the nitrous acid derivative, a larger excess of the nitrosylating agent doing no harm. It is often advantageous to use a one molar to two molar excess if sodium nitrite is employed. Reaction temperatures can range from about −10 to about +30°C, especially from about 10°to about 20°C. The coumaranedione-monoxime solidifies as a precipitate and can be isolated by filtration if desired.

The coumaranedione-monoxime is then catalytically hydrogenated in the presence of an acid anhydride. The coumaranedione-monoxime can be employed in the crude form obtained in the first stage or in purified form. The hydrogenation can be conducted in a polar solvent such as an ether, for example dioxane, tetrahydrofuran or ethylene glycol dimethyl ether; dimethylformamide, tetramethylenesulfone, N-methylpyrrolidone, or an aliphatic carboxylic acid having up to 6 carbon atoms such as acetic acid or propionic acid. Mixtures of solvents can also be used. Catalysts which can be used include Raney catalysts such as Raney nickel or noble metal catalysts, for example palladium or platinum catalysts which can be precipitated on the customary supports. Supported palladium contact catalysts such as palladium-on-charcoal, aluminium oxide or barium sulfate are particularly suitable. Preferred acid anhydrides of Formula IV are the anhydrides of lower aliphatic carboxylic acids with 2 to 4 carbon atoms, such as acetic anhydride and propionic anhydride. Acetic anhydride is preferably used but the nature of $R^1$ and $R^2$ is not critical.

The reaction temperatures are generally between about 20°and about 100°C, especially from about 50° to about 80°C. Although the hydrogenation can be conducted at atmospheric pressure, it is preferably carried out at pressures of from about 5 to about 100 bars, preferably 40 to 60 bars, of hydrogen.

The amidocoumaranone which is obtained in the second stage, is isolated by removing the catalyst, evaporating the solvent, and purifying the reaction product by trituration with a solvent in which it is sparingly soluble, such as ethyl acetate or diethyl ether.

The resulting amidocoumaranone of Formula V is then hydrolyzed with an aqueous mineral acid such as hydrochloric acid, hydrobromic acid or sulfuric acid. The concentration of the acid is not critical and can vary from about 1N to about 10N, depending on the acid. Preferably, the concentration is between 2 and 4N. Typically, 1 mole of the corresponding amidocoumaranone is hydrolyzed with at least 2 moles of acid. Reaction temperatures are generally from about 60° to about 120°C, preferably 90° to about 100°C. The reaction time depends on the temperature. At 90°C, it is about 4 hours. Above 100°C, the reaction can be carried out under pressure. The solution resulting from hydrolysis is concentrated in vacuo and neutralized with an aqueous alkali metal hydroxide solution, such as potassium hydroxide solution, sodium hydroxide solution, or with ammonia. The α-amino-2-hydroxyphenylacetic acid is obtained directly in a highly pure form. It can, if desired, be purified further as by recrystallization, for example from water.

The product produced by the process of the invention is asymmetric and can be resolved into its optical antipodes by conventional means, e.g. salt formation with camphorsulfonic acid or other optically active acids.

The α-aminohydroxyphenylacetic acids thus produced are suitable for the manufacture of certain antibiotics, including the cephalosporin derivatives of Canadian Patent Specification 873,869. In addition, the α-amino-2-hydroxyphenylacetic acid can be used to convert 6-aminopenicillanic acid into the highly active penicillin, 6-(α-amino-2-hydroxyphenyl acetamido)-penicillanic acid through any of the well known acylation techniques. Since the penicillin formed with the R-form of α-amino-2-hydroxyphenylacetic acid is outstandingly effective, resolution as described above is preferably performed before acylation.

The following examples will serve to further typify the nature of this invention without being a limitation on the scope thereof, the scope being defined solely by the appended claims.

EXAMPLE 1

α-Amino-2-Hydroxyphenylacetic Acid

A. To a solution of 134 parts by weight of 2-hydroxyphenylacetic acid lactone in 1000 parts by volume of glacial acetic acid are slowly added 210 parts by weight of sodium nitrite at 10° to 20°C. The reaction mixture is stirred for 4 hours at 15° to 20°C and is subsequently poured into 3 litres of ice water. The reaction product is collected by filtration, washed with water and dried over potassium hydroxide to yield 140 parts by weight of coumaranedione-3-monoxime, m.p. 176°–182°C (dec).

B. A solution of 147 parts by weight of coumaranedione-3-monoxime in 450 parts by volume of glacial acetic acid and 450 parts by volume of acetic anhydride is catalytically hydrogenated with 15 g of 5% palladium-on-charcoal at 60°C under a pressure of 40 to 60 bars of hydrogen. The catalyst is removed by filtation, the filtrate is evaporated and 118 parts by weight of 3-acetamidocoumaran-2-one are obtained by triturating the evaporation residue with ether, m.p. 177°–182°C (dec).

C. Ninety-six parts by weight of 3-acetamidocoumaran-2-one are hydrolyzed with 1300 parts by volume of 3N hydrochloric acid for 4 hours at 95°C. The solution is concentrated to approximately 300 parts by volume and rendered neutral to Congo Red with concentrated ammonia solution. The α-amino-2-hydroxyphenylacetic acid which thus solidifies is collected by filtration, washed with water and dried in vacuo at 70°C. The yield is 65 parts by weight; melting point: 190°–191°C (dec).

EXAMPLE 2

α-Amino-2-Hydroxy-5-Chlorophenylacetic Acid

A. A solution of 47.6 parts by weight of 2-hydroxy-5-chlorophenylacetic acid lactone in 560 parts by volume of glacial acetic acid is treated with 59.2 parts by weight of sodium nitrite at 10°C to 20°C. The reaction mixture is stirred for 4 hours at 15°to 20°C and poured into 1700 parts by volume of ice water. The reaction product is collected by filtration, washed with water and dried in vacuo over potassium hydroxide to yield 51.5 parts by weight of 5-chlorocoumaranedione-3-monoxime, m.p. 192°C (dec).

B. Fifty parts by weight of 5-chlorocoumaranedione-3-monoxime in 500 parts by volume of dioxane and 150 parts by volume of acetic anhydride are catalytically hydrogenated with 5 g of 5% palladium-on-charcoal at 70° to 80°C in a fashion analogous to that described in Example 1B to yield 31.1 parts by weight of 3-acetamido-5-chlorocoumaranone, m.p. 197°–199°C (dec).

C. A mixture of 22.5 parts by weight of 3-acetamido-5-chlorocoumaran-2-one, 267 parts by volume of 3N hydrochloric acid and 200 parts by volume of dioxane are heated under reflux for 4 hours. The solution is evaporated and the residue is taken up in a 4-fold amount of water and treated with 50 parts by volume of 2N sodium hydroxide solution. The α-amino-2-hydroxy-5-chlorophenylacetic acid which solidifies is collected by filtration, washed with water and dried to yield 17.8 parts by weight of product, m.p. 186°187°C (dec).

In a similar fashion, α-amino-2-hydroxy-5-methylphenylacetic acid is obtained from 2-hydroxy-5-methylphenylacetic acid lactone.

We claim:

1. A compound of the formula:

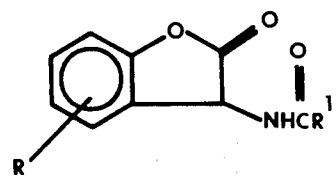

wherein R is hydrogen, halo or alkyl of 1 to 4 carbon atoms and $R^1$ is alkyl of 1 to 4 carbon atoms.

2. The compound of claim 1 wherein R is hydrogen, chloro or methyl and $R^1$ is methyl.

3. The compound of claim 1 wherein R is hydrogen and $R^1$ is methyl.

4. The compound of claim 1 wherein R is chloro in the 5-position of the coumarane ring and $R^1$ is methyl.

5. The compound of claim 1 wherein R is methyl in the 5-position of the coumarane ring and $R^1$ is methyl.

* * * * *